(12) United States Patent
Nakatani et al.

(10) Patent No.: US 9,789,059 B2
(45) Date of Patent: Oct. 17, 2017

(54) ORAL DISINTEGRATING TABLET

(71) Applicant: Boehringer Ingelheim International GmbH, Ingelheim am Rhein (DE)

(72) Inventors: Manabu Nakatani, Hyogo (JP); Yohei Kawabata, Yamagata (JP); Takeshi Sawada, Osaka (JP); Hiroshi Takasaki, Hyogo (JP)

(73) Assignee: Boehringer Ingelheim International GmbH, Ingelheim am Rheim (DE)

( * ) Notice: Subject to any disclaimer, the term of this patent is extended or adjusted under 35 U.S.C. 154(b) by 0 days.

(21) Appl. No.: 14/811,992

(22) Filed: Jul. 29, 2015

(65) Prior Publication Data

US 2016/0030336 A1 Feb. 4, 2016

(30) Foreign Application Priority Data

Jul. 30, 2014 (EP) .................................. 14179147

(51) Int. Cl.
*A61K 9/20* (2006.01)
*A61K 9/00* (2006.01)
*A61K 31/4184* (2006.01)

(52) U.S. Cl.
CPC .......... *A61K 9/0056* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 9/2081* (2013.01); *A61K 9/2095* (2013.01); *A61K 31/4184* (2013.01)

(58) Field of Classification Search
None
See application file for complete search history.

(56) References Cited

U.S. PATENT DOCUMENTS

| 9,119,820 B2 | 9/2015 | Fukushima et al. |
| 2005/0186274 A1* | 8/2005 | Kohlrausch ............ A61K 9/209 424/464 |
| 2009/0030057 A1 | 1/2009 | Wizel et al. |
| 2016/0030336 A1 | 2/2016 | Nakatani et al. |

FOREIGN PATENT DOCUMENTS

| WO | 2004028505 A1 | 4/2004 |
| WO | 2007061415 A1 | 5/2007 |
| WO | 2014091263 A1 | 6/2014 |

OTHER PUBLICATIONS

International Search Report for PCT/EP2015/067321 mailed on Sep. 17, 2015.
Park et al. "Comparative Study of Telmisartan Tablets Prepared via the Wet Granulation Method and Pritor (TM) Prepared Using the Spray-Drying Method" (2011) Archives of Pharmacal Research, vol. 34, No. 3, pp. 463-468.

* cited by examiner

*Primary Examiner* — Susan Tran
(74) *Attorney, Agent, or Firm* — Marc Began; Paula K. Wittmayer

(57) ABSTRACT

A process for the preparation of an oral disintegrating tablet comprising the antihypertensive telmisartan and the tablet obtained by the process.

12 Claims, No Drawings

ORAL DISINTEGRATING TABLET

The present invention relates to a process for the preparation of a tablet comprising the antihypertensive telmisartan and an oral disintegrating tablet produced by the method.

BACKGROUND OF THE INVENTION

Telmisartan is an angiotensin II receptor antagonist developed for the treatment of hypertension and other medical indications as disclosed in EP-A-502314. Its chemical name is 4'-[2-n-propyl-4-methyl-6-(1-methylbenzimidazol-2-yl)-benzimidazol-1-ylmethyl]-biphenyl-2-carboxylic acid having the following structure:

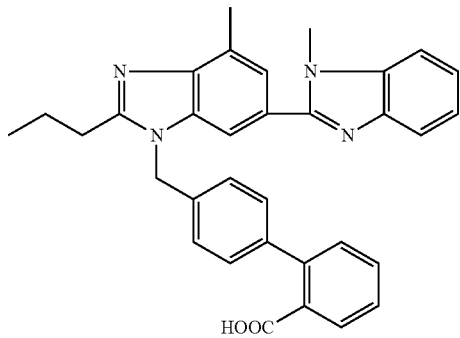 [SMILES: CCCc1nc2c(C)cc(-c3nc4ccccc4n3C)cc2n1Cc1ccc(-c2ccccc2C(=O)O)cc1]

Telmisartan is manufactured and supplied in the free acid form. It is characterized by its very poor solubility in aqueous systems at the physiological pH range of the gastro-intestinal tract between pH 1 to 7. As disclosed in WO 00/43370, crystalline telmisartan exists in two polymorphic forms having different melting points. Under the influence of heat and humidity, the lower melting polymorph B transforms irreversibly into the higher melting polymorph A.

An oral disintegrating tablet (ODT) is a solid pharmaceutical dosage form which rapidly dissolves or disintegrates in the mouth without water or chewing.

OBJECT OF THE INVENTION

By providing a process for the preparation of telmisartan tablets with properties of oral disintegration the present invention facilitates compliance of patients who have difficulties in swallowing telmisartan tablets or patients with limited water intake.

SUMMARY OF THE INVENTION

In accordance with the present invention a second granulation of telmisartan granulate in the presence of corn starch and subsequent blending of the granulate with microcrystalline cellulose and a disintegrant allows, using external lubrication for the compression of tablets, which show oral disintegration.

DESCRIPTION OF THE INVENTION

The present invention refers to a process for the preparation of telmisartan tablets comprising
(a) spraying an aqueous solution of telmisartan, a basic agent and a surfactant on to a first filler and a flow control agent to obtain a first granulate, and drying the granulate;
(b) coating the first granulate together with a coating agent such as corn starch to obtain a second granulate;
(c) drying and screening (i.e. sieving to ensure de-agglomeration) said second granulate;
(d) blending the screened granulate with a second filler and a disintegrant; and
(e) tableting the blend using external lubrication in the presence of a lubricant.

Telmisartan tablets authorized in Japan show an erosion type slow disintegration. Granules containing telmisartan are produced in a fluid bed granulator by spraying a telmisartan, meglumine and poloxamer solution onto further excipients resulting in telmisartan granules having sticky properties and good compressibility.

Unexpectedly, the present invention is able to improve the slow tablet disintegration by a second fluid bed granulation process step adding corn starch, which coats the granule surface and reduces the sticky properties of the first granulate. To achieve a good content uniformity (CU) controlling the particle size of the coated granules turned out to be beneficial.

Finally, with the optional addition of microcrystalline cellulose and crospovidone the compressibility of the coated granules can surprisingly be improved.

An even further reduction of the oral disintegration time can be achieved using external lubrication with a lubricant such as magnesium stearate during tableting.

The active ingredient telmisartan is generally supplied in its free acid form, although pharmaceutically acceptable salts such as the sodium salt may also be used.

Specific examples of suitable basic agents are alkali metal hydroxides such as NaOH and KOH; basic amino acids such as arginine and lysine; and meglumine (N-methyl-D-glucamine), meglumine being preferred.

The surfactants and emulsifiers may be ionic or non-ionic, the latter being preferred. Examples are poloxamers and pluronics. Suitable poloxamers have an average molecular weight of 6000 to 10000. Specific examples of poloxamers are poloxamer 182LF, poloxamer 188 and poloxamer 331.

The first filler is selected from the group consisting of cellulose, dibasic calcium phosphate anhydrous, erythritol, mannitol, microcrystalline cellulose, and pregelatinized starch. A preferred first filler is erythritol.

The coating agent is selected from corn starch, pregelatinized starch, lactose, D-mannitol, erythritol or microcrystalline cellulose.

The second filler for blending with the coated granules is selected from the group consisting of cellulose, erythritol, mannitol, microcrystalline cellulose and pregelatinized starch. A preferred second filler is microcrystalline cellulose.

Suitable flow control agents are anhydrous silicic acid, colloidal silicon dioxide and talc. Particularly preferred is light anhydrous silicic acid and in particular Silica, Colloidal Anhydrous.

The disintegrant is selected from the group consisting of sodium starch glycolate, crospovidone (cross-linked polyvinylpyrrolidone), corn starch and pregelatinized starch. A preferred disintegrant is crospovidone Suitable lubricants are sodium stearyl fumarate and magnesium stearate, the latter being preferred.

Preferably, in process step (a) of the above process a fluid bed granulator is used, which can optionally be used for drying of the first granulate as well. Alternatively, a tray dryer can be used for drying the first granulate.

If a fluid bed granulator is used in process step (a) the second granulate can be obtained in process step (b) by putting corn starch in the fluid bed granulator and granulating the first granulate together with the corn starch by spraying water. Alternatively, an aqueous corn starch suspension could be sprayed in process step (b) on to the first granulate in the fluid bed granulator.

Subsequently, the second granulate could be dried either in the fluid bed granulator or in a tray drier.

A further embodiment of the present invention is an oral disintegrating tablet comprising 20-80 mg angiotensin II receptor antagonist telmisartan;
20-80 mg basic excipient selected from the group consisting of alkali metal hydroxides, basic amino acids and meglumine such as 2-33 mg NaOH or 3-46 mg KOH or 4-80 mg $NaHCO_3$, $KHCO_3$, $Na_2CO_3$, $K_2CO_3$, $Na_2HPO_4$ or $K_2HPO_4$;
20-350 mg filler selected from the group consisting of cellulose, dibasic calcium phosphate anhydrous; erythritol, mannitol, microcrystalline cellulose and pregelatinized starch;
20-150 mg coating agent of the first granulate selected from corn starch, pregelatinized starch, lactose, D-mannitol, erythritol or microcrystalline cellulose;
5-50 mg disintegrant selected from the group consisting of sodium starch glycolate, crospovidone, corn starch and pregelatinized starch;
2-20 mg surfactant/emulsifier poloxamer 188;
0.5-10 mg sweetener;
0.12-1.2 mg flow control agent light anhydrous silicic acid;
0.01-1.0 mg lubricant; and
0.01-1.0 mg dye or pigment.

Said tablet has a weight of 150-740 mg, preferably 300-700 mg and more preferably about 340 or 680 mg.

Thus, the tablet comprises
3 to 50 wt. %, preferably 5 to 35 wt. %, of telmisartan;
0.25 to 20 wt. %, preferably 0.40 to 15 wt. %, of basic agent; and
30 to 95 wt. %, preferably 10 to 80 wt. % of filler
1-50 wt %, preferably 5-25 wt % disintegrant
0.1-10 wt %, preferably 10 wt % surfactant such as poloxamer 188
0.1-5 wt %, preferably 0.5-2 wt % sweetener
0.01-1 wt %, preferably 0.05-0.5 wt % flow control agent
below 0.1 wt %, i.e traces of lubricant and
below 0.1 wt %, i.e. traces of a dye or pigment Other (optional) constituents may, for instance, be chosen from one or more of the following excipients and/or adjuvants in the amounts indicated:
1 to 10 wt. %, preferably 2 to 8 wt. %, of crystallization retarders;
1 to 10 wt. %, preferably 2 to 8 wt. %, of solubilizers;
0.5 to 10 wt. %, preferably 2 to 8 wt. %, of pH control agents;

The tablet contains 10-160 mg amorphous telmisartan, preferably 20-80 mg or 40-80 mg.

A preferred basic excipient is meglumine;
Preferred fillers are erythritol and microcrystalline cellulose;
Preferred disintegrants are crospovidone (cross-linked polyvinylpyrrolidone), corn starch and pregelatinized starch;
Preferred lubricant is magnesium stearate;
A preferred sweetener is saccharin sodium; Preferred dyes or pigments are iron oxides such as iron oxide black.

The tablets obtained according to the invention disintegrate rapidly (e.g. within 10-30 seconds).

To minimize hygroscopicity of the tablets of the present invention they can be packaged using a moisture-proof packaging material such as PVC/PVDC blister in aluminium pouch, aluminium sachet or glass bottles, polypropylene tubes and HDPE bottles which preferably contain a desiccant.

A method described above can be used for the manufacture of an oral disintegrating tablet according to the present invention to treat hypertension either alone or in combination with the treatment or prevention of a condition selected from the group consisting of chronic stable angina, vasospastic angina, stroke, myocardial infarction, transient ischemic attack, congestive heart failure, cardiovascular disease, diabetes, insulin resistance, impaired glucose tolerance, prediabetes, type 2 diabetes mellitus, diabetic nephropathy, metabolic syndrome (syndrome X), obesity, dyslipidemia, hypertriglyceridemia, elevated serum concentrations of C-reactive protein, elevated serum concentrations of lipoprotein(a), elevated serum concentration of homocysteine, elevated serum concentration of low-density lipoprotein (LDL)-cholesterol, elevated serum concentration of lipoprotein-associated phospholipase (A2), reduced serum concentration of high density lipoprotein (HDL)-cholesterol, reduced serum concentration of HDL(2b)-cholesterol, reduced serum concentration of adiponectin, cognitive decline and dementia.

Particularly preferred is the additional treatment or prevention of chronic stable angina, vasospastic angina, stroke, myocardial infarction, congestive heart failure, diabetes, dyslipidemia or dementia.

In addition to lowering elevated blood pressure (hypertension) the tablet can be used in a method to treat or prevent chronic stable angina, vasospastic angina, stroke, myocardial infarction, congestive heart failure, diabetes, dyslipidemia or dementia.

In order to further illustrate the present invention, the following non-limiting examples are given:

EXAMPLES

Example 1: First Granulation of Telmisartan with Surfactant and Basic Agent Preparation of the Granulation Liquid
  Dissolve Poloxamer 188 in purified water with stirring.
  While stirring add meglumine to the solution until a clear solution is obtained.
  Continuing stirring add telmisartan until a homogeneous solution is obtained.
  The resulting solution must be clear.
First Granulation
  Transfer erythritol, light anhydrous silicic acid and pigment into a fluid bed granulator.
  Pre-mix briefly and spray in granulation liquid.
Drying
  After completion of the granulation process dry the granulate.

Example 2: Second Granulation of Telmisartan with Corn Starch

Transfer the granules of example 1, corn starch and pigment into a fluid bed granulator and spray in purified water.

Example 3: Screening of Telmisartan Granulate

Screen the granules of example 2 using a screen with a mesh size of 1-5 mm.

Example 4: Blending of Telmisartan Granulate with Disintegrant

Mix the screened granules of example 3 with microcrystalline cellulose, sweetener, pigment and disintegrant.

Example 5: Tableting Using External Lubrication

Compress the blend obtained in example 4 into tablet with a tablet press equipped with an external lubrication system.

Example 6: 40 mg Telmisartan ODT

| Constituents | mg per tablet | % per tablet |
|---|---|---|
| Telmisartan | 40.000 | 11.76 |
| Meglumine | 40.000 | 11.76 |
| Poloxamer 188 | 8.000 | 2.35 |
| Erythritol | 80.500 | 13.09 |
| Light anhydrous silicic acid | 0.500 | 0.15 |
| Corn starch | 67.000 | 19.71 |
| Microcrystalline cellulose | 119.600 | 35.18 |
| Crospovidone | 24.000 | 5 |
| Saccharin sodium | 3.400 | 1 |
| Magnesium stearate | traces | 0 |
| Iron oxide black | traces | 0 |
| Total | 340.000 | 100.000 |

Example 7: 20 mg Telmisartan ODT

| Constituents | mg per tablet | % per tablet |
|---|---|---|
| Telmisartan | 20.000 | 11.76 |
| Meglumine | 20.000 | 11.76 |
| Poloxamer 188 | 4.000 | 2.35 |
| Erythritol | 22.250 | 13.09 |
| Light anhydrous silicic acid | 0.250 | 0.15 |
| Corn starch | 33.500 | 19.71 |
| Microcrystalline cellulose | 59.800 | 35.18 |
| Crospovidone | 8.500 | 5 |
| Saccharin sodium | 1.700 | 1 |
| Magnesium stearate | traces | 0 |
| Iron oxide black | traces | 0 |
| Total | 170.000 | 100.000 |

Example 8: 80 mg Telmisartan ODT

| Constituents | mg per tablet | % per tablet |
|---|---|---|
| Telmisartan | 80.000 | 11.76 |
| Meglumine | 80.000 | 11.76 |
| Poloxamer 188 | 16.000 | 2.35 |
| Erythritol | 89.000 | 13.09 |
| Light anhydrous silicic acid | 1.000 | 0.15 |
| Corn starch | 134.000 | 19.71 |
| Microcrystalline cellulose | 239.200 | 35.18 |
| Crospovidone | 34.000 | 5 |
| Saccharin sodium | 6.800 | 1 |
| Magnesium stearate | traces | 0 |
| Iron oxide black | traces | 0 |
| Total | 680.000 | 100.000 |

The invention claimed is:

1. A process for the preparation of a telmisartan tablet comprising
   1) (a) spraying an aqueous solution of telmisartan, a basic agent and a surfactant on to a first filler and a flow control agent to obtain a first granulate and drying the granulate;
   2) (b) coating the first granulate with a coating agent selected from the group consisting of corn starch, pregelatinized starch, lactose, D-mannitol, erythritol and microcrystalline cellulose to obtain a coated granulate;
   3) (c) drying and screening the coated granulate;
   4) (d) blending the dried and screened coated granulate with a second filler selected from the group consisting of cellulose, dibasic calcium phosphate anhydrous, erythritol, mannitol, microcrystalline cellulose corn starch, and pregelatinized starch, a flow control agent and a disintegrant selected from the group consisting of sodium starch glycolate, crospovidone, corn starch and pregelatinized starch; and
   5) (e) tableting the blend using external lubrication in the presence of a lubricant.

2. The process according to claim 1 wherein the basic agent is selected from the group consisting of alkali metal hydroxides, basic amino acids, meglumine, NaOH, KOH, NaHCO$_3$, KHCO$_3$, Na$_2$CO$_3$, K$_2$CO$_3$, Na$_2$HPO$_4$ and K$_2$HPO$_4$.

3. The process according to claim 1 wherein the surfactant is selected from the group of non-ionic surfactants.

4. The process according to claim 1 wherein the first filler is selected from the group consisting of cellulose, dibasic calcium phosphate anhydrous, erythritol, mannitol, microcrystalline cellulose, and pregelatinized starch.

5. The process according to claim 1 wherein the flow control agent is light anhydrous silicic acid.

6. The process according to claim 1 wherein in process step (b) the first granulate is coated on the surface with corn starch.

7. The process according to claim 1 wherein the second filler is micro-crystalline cellulose.

8. The process according to claim 1 wherein the disintegrant is selected from the group consisting of sodium starch glycolate, crospovidone, corn starch and pregelatinized starch.

9. The process according to claim 8 wherein the disintegrant is crospovidone.

10. The process according to claim 1 wherein the lubricant is selected from the group consisting of sodium stearyl fumarate and magnesium stearate.

11. The process according to claim 10 wherein the lubricant is magnesium stearate.

12. The process according to claim 1 using a fluid bed granulator in process steps (a) and (b) and drying the granulate in the granulator.

* * * * *